United States Patent [19]

Enders et al.

[11] 4,077,981

[45] Mar. 7, 1978

[54] CERTAIN 1-ALKYL-2-DICHLORO-PHENYLIMINOPYRROLIDINES

[75] Inventors: Edgar Enders, Cologne-Flittard; Wilhelm Stendel, Wuppertal-Vohwinkel, both of Germany

[73] Assignee: Bayer Aktiengesellschaft, Leverkusen, Germany

[21] Appl. No.: 778,642

[22] Filed: Mar. 17, 1977

Related U.S. Application Data

[60] Division of Ser. No. 609,889, Sep. 2, 1975, which is a continuation of Ser. No. 380,774 Jul. 19, 1973, Pat. No. 3,927,217, which is a division of Ser. No. 151,516, Jun. 9, 1971, Pat. No. 3,787,576, which is a division of Ser. No. 834,537, Jun. 18, 1969, abandoned.

[30] Foreign Application Priority Data

Jun. 21, 1968 Germany ............................ 1770681

[51] Int. Cl.$^2$ ............................................ C07D 207/22
[52] U.S. Cl. .................................................. 260/326.85
[58] Field of Search ..................................... 260/326.85

[56] References Cited

U.S. PATENT DOCUMENTS

| 3,189,648 | 6/1965 | Gerjovich | 260/326.85 |
| 3,284,465 | 11/1966 | Scola | 260/326.85 |
| 3,563,994 | 2/1971 | Wollweber | 260/326.85 |

*Primary Examiner*—Alton D. Rollins
*Attorney, Agent, or Firm*—Burgess, Dinklage & Sprung

[57] ABSTRACT

2-phenyliminopyrrolidines, i.e. 1-[alkyl and alkenyl]-2-[di and tri (halo and alkyl substituted)-phenylimino]-[optionally 3-, 4- or 5- alkyl substituted]-pyrrolidines, which possess parasiticidal properties, especially animal acarid ectoparasiticidal properties, and which may be produced by conventional methods.

5 Claims, No Drawings

CERTAIN 1-ALKYL-2-DICHLOROPHENYLIMINOPYRROLIDINES

This is a division of Application Ser. No. 609,899, filed Sept. 2, 1975 now pending, which is a continuation of Ser. No. 380,774, filed July 19, 1973, now U.S. Pat. No. 3,927,217, issued Dec. 16, 1975, which was a division of Ser. No. 151,516, filed June 9, 1971 now U.S. Pat. No. 3,787,576, issued Jan. 22, 1974, which was a division of Ser. No. 834,537, filed June 18, 1969, now abandoned.

The present invention relates to and has for its objects the provision for particular new 2-phenyliminopyrrolidines, i.e. 1-[alkyl and alkenyl]-2-[di and tri (halo and alkyl substituted)-phenylimino]-[optionally 3-, 4- or 5-alkyl substituted]-pyrrolidines, which possess parasiticidal, especially animal acarid ectoparasiticidal properties, active compositions in the form of mixtures of such compounds with solid and liquid dispersible carrier vehicles, and methods for producing such compounds and for using such compounds in a new way especially for combating pests, e.g. parasites, especially animal acarid ectoparasites, with other and further objects becoming apparent from a study of the within specification and accompanying examples.

No phenylimino-pyrrolidines of the type contemplated by the present invention have been heretofore described in the literature, and certainly no such compounds have been suggested as having parasiticidal activity.

It has been found, in accordance with the present invention, that the particular new 2-phenylimino-pyrrolidines of the formula

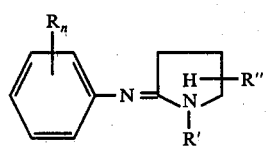

in which
R is chloro, bromo, fluoro or alkyl of 1-4 carbon atoms,
n is a whole number from 2-3, with the proviso that at least one of the substituents R is chloro, bromo or fluoro,
R' is alkyl of 1-6 or 2-6 carbon atoms, or alkenyl of 3-4 carbon atoms, and
R'' is hydrogen or alkyl of 1-4 carbon atoms,
exhibit strong pesticidal, especially animal acarid ectoparasiticidal, properties.

It has been furthermore found, in accordance with the present invention, that the compounds of formula (I) above may be produced by the process which comprises condensing an aniline of the formula

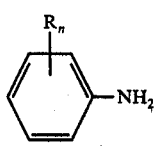

in which R and n are the same as defined above, with a pyrrolidone of the formula

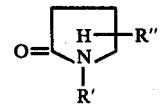

in which R' is alkyl of 1-6 or 2-6 carbon atoms, or alkenyl of 3-4 carbon atoms, and R'' is the same as defined above, in the presence of an agent which splits off water, and isolating the product thereby produced in the form of the corresponding halogen hydracid salt or in free form and, optionally, then converting the same into any other desired salt.

Advantageously, the particular new compounds of formula (I) are distinguished by outstanding animal acarid ectoparasiticidal properties, especially against resistant strains of such parasites as well as extremely low toxicity to warm-blooded animals. In contrast thereto, the previously known phosphoric acid esters and carbamates used to combat such parasites, are less effective because resistance builds up in initially susceptible parasites of the foregoing kind to such known compounds. The new compounds of the present invention therefore represent a genuine enrichment of the art.

If 3,4-dichloro-aniline and N-butyl-pyrrolidone-(2) are used as starting materials, the reaction course can be represented by the following formula scheme:

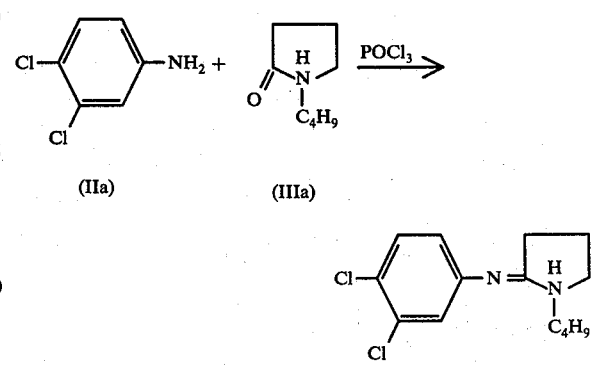

(7)

Advantageously, in accordance with the present invention, in the various formulae herein:
R represents
chloro;
bromo;
fluoro; and/or
straight and branched chain lower alkyl of 1-4 carbon atoms such as methyl, ethyl, n- and iso-propyl, n-, iso-, sec.- and tert.-butyl, and the like, especially $C_{1-3}$ or $C_{1-2}$ alkyl, and more especially methyl and ethyl;
n represents
a whole number from 2 to 3, especially 2; with the proviso that at least one of the substituents R is chloro, bromo or fluoro, whereby $R_n$ includes 2 or 3 (same or different) substituents, i.e. chloro, bromo and/or fluoro, and optionally $C_{1-4}$ alkyl hydrocarbon;
R' represents
straight and branched chain alkyl hydrocarbon of 1-6 carbon atoms such as methyl to tert.-butyl inclusive as defined above, amyl, n-hexyl, pinacolyl (i.e. [CH$_3$]$_3$C—[CH$_3$]CH—), and the like, especially C$_{2-6}$ or C$_{2-4}$ alkyl; or straight and branched chain alkenyl hydrocarbon of 3 to 4 carbon atoms such as α-, β- and γ- allyl (i.e. prop-1 and 2-enyl and 1-methyl-vinyl), but- 1,2 and 3-enyl, and the like, especially α-allyl and but-2-enyl; and R" represents
hydrogen; or
straight and branched chain lower alkyl hydrocarbon of 1-4 carbon atoms such as methyl to tert.-butyl inclusive as defined above, and the like, especially C$_{1-3}$ or C$_{1-2}$ alkyl, more especially 5-position substituted C$_{1-3}$ or C$_{1-2}$ alkyl, and most especially methyl.

Preferably, R$_n$ is dichloro, trichloro, dibromo, (C$_{1-4}$ alkyl)-(chloro), (C$_{1-4}$ alkyl)-(bromo), chloro-bromo, chloro-fluoro, or bromo-fluoro; R' is C$_{2-4}$ alkyl, or C$_{3-4}$ alkenyl; and R" is hydrogen, or C$_{1-4}$ or C$_{1-2}$ alkyl.

In particular, R$_n$ is 2,3-, 2,4-, 2,5- and 3,4-dichloro, 2,4,5-trichloro, 2,4- and 3,4-dibromo, 2-chloro-4-bromo, 2-bromo-4-chloro, 3-chloro-4-bromo, 3-bromo-4-chloro, 2-chloro-4-fluoro, 3-chloro-4-fluoro, 2-methyl-4-chloro, 3-methyl-4-chloro, 3-chloro-4-methyl, 2-bromo-4-fluoro, 3-bromo-4-fluoro, 2-methyl-4-bromo, and 2-ethyl-4-bromo.

The aniline starting materials of formula (II) above are known.

As examples of preferred anilines usable as starting materials herein, there are mentioned:

| | |
|---|---|
| 2,4-dichloro-aniline | 4-fluoro-3-chloro-aniline |
| 3,4-dichloro-aniline | 2,4-difluoro-5-chloro-aniline |
| 2,4,5-trichloro-aniline | 4-fluoro-2-methyl-aniline |
| 2,4,6-trichloro-aniline | 2-chloro-4-bromo-aniline |
| 3,4,5-trichloro-aniline | 4-chloro-2-bromo-aniline |
| 2,3,4-trichloro-aniline | 2,4-dibromo-aniline |
| 4-chloro-2-methyl-aniline | 4-bromo-2-methyl-aniline |
| 2-chloro-4-methyl-aniline | 4-fluoro-2-bromo-aniline |
| 2,4-dichloro-5-methyl-aniline | 2,5-dichloro-4-bromo-aniline |
| 2,4-difluoro-aniline | 4,5-dichloro-2-bromo-aniline |
| 4-fluoro-2-chloro-aniline | 2-fluoro-4-bromo-aniline |
| 4-chloro-2-fluoro-aniline | 4-bromo-2-ethyl-aniline |
| 4-chloro-2-ethyl-aniline | 4-bromo-2-isopropyl-aniline |

The pyrrolidones of formula (III) above usable as starting materials are also known.

Pyrrolidones which are suitable for the production process according to the present invention, include in particular:

| | |
|---|---|
| | N-n-butyl-pyrrolidone-(2) |
| N-ethyl-pyrrolidone-(2) | N-sec.-butyl-pyrrolidone-(2) |
| N-n-propyl-pyrrolidone-(2) | N-tert.-butyl-pyrrolidone-(2) |
| N-isopropyl-pyrrolidone-(2) | N-isobutyl-pyrrolidone-(2) |
| N-allyl-pyrrolidone-(2) | N-n-pentyl-pyrrolidone-(2) |
| N-n-hexyl-pyrrolidone-(2) | 1,3-dimethyl-pyrrolidone-(2) |
| 1-5-dimethyl-pyrrolidone-(2) | N-crotyl-pyrrolidone-(2) |
| 1-ethyl-5-methyl-pyrrolidone-(2) | N-methylallyl-pyrrolidone-(2) |
| 1-propyl-5-methyl-pyrrolidone-(2) | N-(buten-(3)-yl)-pyrrolidone-(2) |

The production reaction can be carried out, if desired, in the presence of an inert solvent (the term solvent including mere diluents). Suitable solvents are aromatic hydrocarbons, such as benzene, toluene and xylene, and chlorinated hydrocarbons, such as chlorobenzene, dichlorobenzenes and tetrachloroethylene, and the like.

As agents which split off water, inorganic acid halides are preferably used, such as phosphorus oxychloride, thiophosphoryl chloride, phosphorus trichloride, thionyl chloride, phosgene, silicon tetrachloride, stannous tetrachloride, and the like.

The reaction temperatures which may be used can be varied advantageously within a fairly wide range. In general, the reaction is carried out at substantially between about 10°-130° C, preferably from between about 20°-120° C.

When carrying out the instant production process, the two starting materials are normally used in about equimolar amounts and an equimolar amount of the agent which splits off water is added.

In general, all the reactants are added together and only then is the reaction mixture heated to higher temperatures, for example 100°-120° C. The reaction is complete when the evolution of halogen hydride has ceased.

The instant 2-phenylimino-pyrrolidines are obtained as halogen hydracid salts which are sparingly soluble in organic solvents. The compounds can be isolated as such. For purification, the instant free bases can be liberated by treatment with an aqueous solution of sodium hydroxide or of potassium hydroxide and then distilled.

Advantageously, the instant free bases can be reacted with the appropriate acids to produce any desired salt, for example with inorganic acids, such as sulfuric acid, hydrochloric acid, phosphoric acid, or with organic acids, such as acetic acid, tartaric acid, citric acid, benzenesulfonic acid, and the like.

Advantageously, the instant 2-phenylimino-pyrrolidines and their corresponding salts exhibit strong acaricidal properties, particularly against acarids which as animal ectoparasites infest domesticated animals or live stock such as cattle, sheep, rabbits, and the like. At the same time, the instant active compounds show only a low toxicity to warm-blooded animals. Such compounds are therefore well suited for the control of acarid animal ectoparasites.

As economically important ectoparasites of this nature contemplated herein, particularly in tropical and sub-tropical countries, there are mentioned for example: the Australian and South American cattle tick *Boophilus microplus*, the South African cattle tick *Boophilus decolaratus*, both of the family of the Ixodidae, and the like. In the same manner, representatives of the Sarcoptidae family such as the rabbit sucking-mite (*Psoroptes cuniculi*), and the like, can also be controlled.

Further ectoparasites of the order Acarida with great economical importance, which live in the Tropics, Subtropics or in the temperate zones, are for example:

From the family Ixodidae: The single host cattle tick of Central America, *Boophilus annulatus;* the multi-host brown-ear-tick of sheep and cattle, *Rhipicephalus appendiculatus;* the red-legged tick of sheep and cattle, *Rhipicephalus evertsi;* the bont tick of sheep and cattle, *Amblyomma hebraeum;* the bont-legged tick, *Hyalomma truncatum.*

From the family Sarcoptidae: The sheep-scab mite Psoroptes ovis.

From the family Dermanyssidae: The red-poultry mite *Dermanyssus gallinae.*

The compounds according to the present invention show surprisingly a high activity not only against the single host ticks, for instance the above-mentioned ticks of that type, but also against the multi host ticks, for instance the above-mentioned ticks of that type.

In the course of time, ticks in particular have become resistant against the known phosphoric acid esters and carbamates hitherto used as active agents, for their control, so that successful control in many areas is becoming more and more doubtful. To secure economic cattle husbandry in the infestation areas, there exists an urgent need for active agents which can control all development stages, that is larvae, nymphs, metanymphs, and adults, even of resistant strains, for example of the genus Boophilus. In this regard, up to now in Australia, for instance, the Ridgeland strain and the Biarra strain of *Boophilus microplus* are resistant to a great extent against the appropriate known phosphoric acid ester active agents.

The active compounds according to the present invention are equally effective against the normally sensitive, as well as the resistant, strains, for example of Boophilus. Such active compounds act, on the usual application to the host animal, not only directly lethally on all forms parasitic on the animal but also strongly ovicidally on the adult forms, so that the propagation cycle of the ticks is interrupted both in the parasitic phase on the animal and in the non-parasitic phase. Thus, the laying of eggs is substantially prevented, and the development and hatching of eggs are inhibited.

The active compounds according to the instant invention can be utilized, if desired, in the form of the usual formulations or compositions with inert conventional pesticidal diluents or extenders, i.e. conventional pesticidal dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticidal dispersible liquid diluent carriers and/or dispersible solid carriers optionally with the use of carrier vehicle assistants, e.g. conventional pesticidal surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carrier, including inert organic solvents, such as aromatic hydrocarbons (e.g. benzene, toluene, xylene, etc.), halogenated, especially chlorinated, aromatic hydrocarbons (e.g. chlorobenzenes, such as o-dichlorobenzene, trichlorobenzene, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), pyrrolidones (e.g. N-methyl-pyrrolidone-2), sulfoxides (e.g. dimethyl sulfoxide, etc.), ketones (e.g. acetone, etc.) and/or water; as well as inert dispersible finely divided solid carrier, such as ground natural minerals (e.g. kaolins, alumina, silica, chalk, i.e. calcium carbonate, talc, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic and/or cationic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, quaternary ammonium salts of longer, e.g. $C_{6-20}$ alkyl radicals, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially hygiene control or disinfectant agents, such as other parasiticides, or acaricides, insecticides, fungicides, bactericides, etc. if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or animal, e.g. livestock, application generally contemplate those in which the active compound is present in an amount substantially between about 0.001–5%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001–95%, and preferably 0.01–95%, by weight of the mixture.

It will be appreciated that the application concentrations are produced in connection with the above noted formulations normally by dilution with water. Futhermore, such concentrations can, according to the application form, be varied within a fairly wide range and are generally substantially between about 10 to 50,000 p.p.m. (g/g), preferably between about 100 to 10,000 p.p.m., i.e. 0.001–5%, preferably 0.01–1% as aforesaid.

Advantageously, the aqueous solutions or emulsions of the instant active compounds possess a markedly good stability under practical conditions, so that, even after standing for long periods as a pH in the range of from 7–9, such compounds may remain effective, i.e. even for 3 months or longer.

In particular, the present invention contemplates methods of selectively killing, combating or controlling pests, e.g. parasites, i.e. animal acarid ectoparasites, which comprises applying to at least one of correspondingly (a) such animal acarid ectoparasites, and (b) the corresponding habitat, i.e. the locus to be protected, e.g. the animal or livestock, a correspondingly combative or toxic amount, i.e. animal acarid ectoparasiticidally effective amount of the particular active compound of the invention alone or together with a carrier vehicle as noted above. The instant formulations or compositions are applied in the usual manner, for instance by spraying, atomizing, scattering, dusting, watering, i.e. as a bath (dip), sprinkling, pouring, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention is illustrated, without limitation, by the following examples:

EXAMPLE 1

In-vitro Test for Ovicidal Effect on Ticks 3 g of the particular active compound are mixed with 7 g of a mixture of equal parts by weight of ethyleneglycol monomethyl ether and nonylphenyl polyglycol ether. The emulsion concentrate so obtained is diluted with water to the application concentration desired in each case.

Adult, fully engorged female ticks of the species *Boophilus microplus* (resistant) are immersed for 1 minute in this preparation of the given active compound. After immersion of, in each case, 10 female specimens of the various strains of ticks, the individual ticks are transferred to plastic dishes, the bottom of each of which is covered with a disc of filter paper. As a control, similar ticks of a normally sensitive strain are treated in exactly the same manner.

After 35 days, the effectiveness of the preparation of the given active compound is determined by ascertaining the inhibition of the depositing of fertile eggs compared with the egg depositing of untreated control ticks. The effect is stated in %, 100% meaning that fertile eggs ceased to be deposited, and 0% signifying that the ticks have deposited eggs in normal manner like the untreated control ticks.

The following Tables 1a and 1b demonstrate the ovicidal effect of the particular active compounds in accordance with the present invention.

Table 1a

| In-vitro test for ovicidal effect on ticks | | |
|---|---|---|
| Active compound: 1-methyl-2-(2',4'-dichloro-phenylimino)-pyrrolidine ($l_1$) | | |
| Parasite: Boophilus microplus | Concentration of active compound in % | Inhibition of egg depositing in % |
| Ridgeland strain resistant | 1.0 | 100 |
|  | 0.3 | 100 |
|  | 0.1 | 100 |
|  | 0.03 | >50 |
|  | 0.01 | 0 |
| Biarra strain resistant | 1.0 | 100 |
|  | 0.3 | 100 |
|  | 0.1 | 100 |
|  | 0.03 | >50 |
|  | 0.01 | 0 |
| normally sensitive strain | 1.0 | 100 |
|  | 0.3 | 100 |
|  | 0.1 | 100 |
|  | 0.03 | >50 |
|  | 0.01 | 0 |

Table 1b

In-vitro test for ovicidal effect on ticks

| Active compound | Physical constant | Ovicidal effect against Boophilus, Biarra strain 100% Inhibition with the stated concentration of active compound | >50% Inhibition (% by weight) |
|---|---|---|---|
| ($2_1$) Cl-phenyl(Cl)-N=pyrrolidine-$C_2H_5$ | b.p. 146–150° C/0.6 mm Hg | 0.1 | 0.01 |
| ($3_1$) Cl,Cl,Cl-phenyl-N=pyrrolidine-$C_2H_5$ | b.p. 165–169° C/0.6 mm Hg | 0.3 | 0.1 |
| ($4_1$) Cl,Cl-phenyl-N=pyrrolidine-$CH_2-CH=CH_2$ | b.p. 169–174° C/0.4 mm Hg | 0.03 | 0.01 |
| ($5_1$) Cl,Cl-phenyl-N=pyrrolidine($CH_3$)-$C_2H_5$ | b.p. 174–177° C/1.7 mm Hg | 0.1 | 0.03 |
| ($6_1$) Cl,Cl-phenyl-N=pyrrolidine-$n$-$C_3H_7$ | b.p. 175–179° C/0.8 mm Hg | 0.03 | 0.01 |
| ($7_1$) Cl,Cl-phenyl-N=pyrrolidine-$n$-$C_4H_9$ | b.p. 179–184° C/0.7 mm Hg | 0.03 | 0.01 |

Table 1b-continued
In-vitro test for ovicidal effect on ticks
| | Active compound | Physical constant | Ovicidal effect against Boophilus, Biarra strain | |
|---|---|---|---|---|
| | | | 100% Inhibition with the stated concentration of active compound | >50% Inhibition (% by weight) |
| (8₁) | 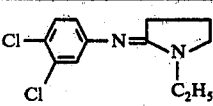 | b.p. 165–170° C/0.6 mm Hg | 0.3 | 0.1 |
| (9₁) | 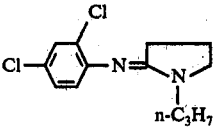 | b.p. 152–157° C/0.3 mm Hg | 0.03 | 0.01 |
| (10₁) | 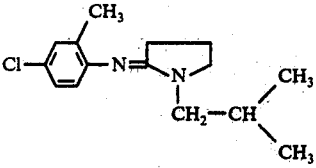 | b.p. 157–162° C/0.5 mm Hg | 0.1 | 0.05 |
| (11₁) | 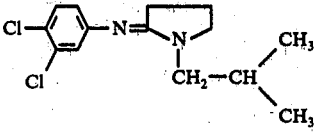 | b.p. 169–171° C/0.4 mm Hg | 0.1 | 0.03 |
| (12₁) | 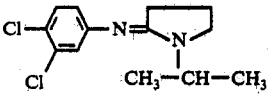 | b.p. 165–170° C/0.5 mm Hg | 0.1 | 0.03 |
| (13₁) | 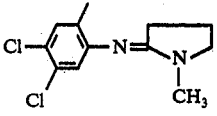 | b.p. 180–184° C/1.5 mm Hg | 0.03 | 0.01 |
| (14₁) | 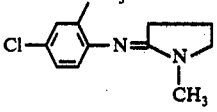 | b.p. 151–157° C/1.3 mm Hg | 0.3 | 0.1 |
| (15₁) | 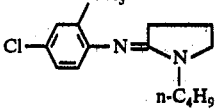 | b.p. 156–160° C/0.5 mm Hg | 0.3 | 0.1 |
| (16₁) | 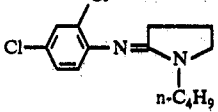 | b.p. 158–162° C/0.5 mm Hg | 0.03 | 0.01 |
| (17₁) | 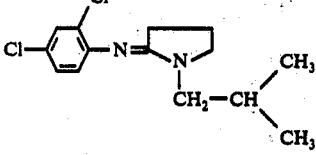 | b.p. 154–156° C/0.5 mm Hg | 0.1 | 0.03 |

Table 1b-continued

In-vitro test for ovicidal effect on ticks

| Active compound | Physical constant | Ovicidal effect against Boophilus, Biarra strain | |
|---|---|---|---|
| | | 100% Inhibition with the stated concentration of active compound | >50% Inhibition (% by weight) |
| (18₁) [2,4-dichlorophenyl, N-tert-butyl pyrrolidine imine] | b.p. 162–164° C/0.5 mm Hg | 0.3 | 0.1 |
| (19₁) [3,4-dichlorophenyl, N-methyl pyrrolidine imine] | b.p. 165–173° C/1.1 mm Hg | 0.3 | 0.1 |
| (20₁) [3,4-dichlorophenyl, N,2-dimethyl pyrrolidine imine] | b.p. 175–178° C/1.5 mm Hg | 0.3 | 0.1 |
| (21₁) [4-chloro-2-methylphenyl, N-n-propyl pyrrolidine imine] | b.p. 153–157° C/0.5 mm Hg | 0.1* | 0.03* |
| (22₁) [2,4-dichlorophenyl, N-isopropyl pyrrolidine imine] | b.p. 158–160° C/1.5 mm Hg | 0.1 | 0.03 |
| (23₁) [4-chloro-2-methylphenyl, N-tert-butyl pyrrolidine imine] | b.p. 143–147° C/0.5 mm Hg | 0.3 | 0.1 |
| (24₁) [4-chloro-2-methylphenyl, N-isopropyl pyrrolidine imine] | b.p. 153–157° C/1.0 mm Hg | 1.0* | 0.3* |

*Ridgeland strain

EXAMPLE 2

The following results were also obtained for further tests carried out in accordance with Example 1.

Table 2

In-vitro test for ovicidal effect on ticks

| Active compound | Physical constant | Ovicidal effect against Boophilum, Biarra strain | |
|---|---|---|---|
| | | 100% Inhibition with the stated concentration of active compound | >50% Inhibition (% by weight) |
| (25₁) [2,4-dibromophenyl, N-methyl pyrrolidine imine] | b.p. 163–165° C/0.3 mm Hg | 0.1 | 0.03 |

Table 2-continued
In-vitro test for ovicidal effect on ticks
| Active compound | | Physical constant | Ovicidal effect against *Boophilum*, ○Biarra strain | |
|---|---|---|---|---|
| | | | 100% Inhibition with the stated concentration of active compound | > 50% Inhibition (% by weight) |
| (26₁) | 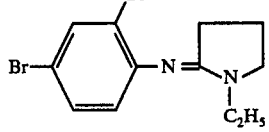 | b.p. 166–170° C/0.3 mm Hg | 0.1 | 0.05 |
| (27₁) | 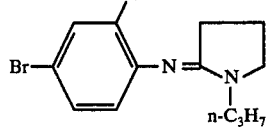 | b.p. 162–167° C/0.3 mm Hg | 0.3 | 0.2 |
| (28₁) | 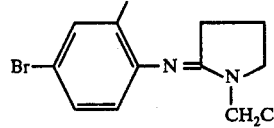 | b.p. 153–158° C/0.01 mm Hg | 0.1 | 0.03 |
| (29₁) | 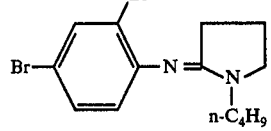 | b.p. 167–171° C/0.2 mm Hg | 0.3 | 0.1 |
| (30₁) | 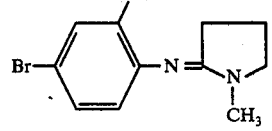 | b.p. 148–153° C/0.2 mm Hg | 0.1 | 0.05 |
| (31₁) | 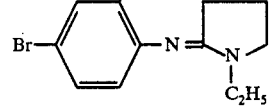 | b.p. 146–152° C/0.2 mm Hg | 0.1 | 0.08 |
| (32₁) | 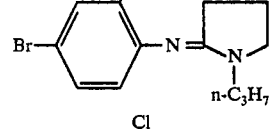 | b.p. 156–162° C/0.2 mm Hg | 0.3 | 0.1 |
| (33₁) | 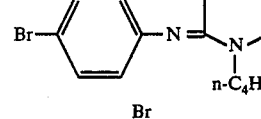 | b.p. 169–176° C/0.2 mm Hg | 0.3 | 0.1 |
| (34₁) | 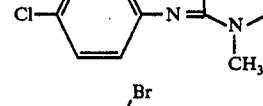 | b.p. 149–153° C/0.2 mm Hg | 0.1 | 0.03 |
| (35₁) | 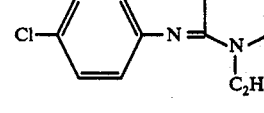 | b.p. 154–157° C/0.2 mm Hg | 0.1 | 0.03 |

Table 2-continued

In-vitro test for ovicidal effect on ticks

| Active compound | Physical constant | Ovicidal effect against *Boophilum*, ○ Biarra strain | |
|---|---|---|---|
| | | 100% Inhibition with the stated concentration of active compound | > 50% Inhibition (% by weight) |
| (36₁) 2-Br, 4-Cl-phenyl, N-n-C₃H₇ pyrrolidine | b.p. 158–162° C/0.2 mm Hg | 0.1 | 0.03 |
| (37₁) 2-Br, 4-Cl-phenyl, N-n-C₄H₉ pyrrolidine | b.p. 163–166° C/0.2 mm Hg | 0.03 | 0.01 |
| (38₁) 2-Br, 4-F-phenyl, N-CH₃ pyrrolidine | b.p. 134–137° C/0.2 mm Hg | 0.3 | 0.1 |
| (39₁) 2-Br, 4-F-phenyl, N-n-C₃H₇ pyrrolidine | b.p. 134–138° C/0.4 mm Hg | 0.03 | 0.02 |
| (40₁) 4-Br, 3-Cl-phenyl, N-C₂H₅ pyrrolidine | b.p. 159–164° C/0.03 mm Hg | 0.1 | 0.08 |
| (41₁) 4-Br, 3-Cl-phenyl, N-CH₂-CH=CH₂ pyrrolidine | b.p. 155–158° C/0.01 mm Hg | 0.3 | 0.1 |
| (42₁) 4-Br, 3-Cl-phenyl, N-n-C₄H₉ pyrrolidine | b.p. 158–160° C/0.01 mm Hg | 0.3 | 0.2 |
| (43₁) 4-Br, 2-CH₃-phenyl, N-CH₂-CH=CH₂ pyrrolidine | b.p. 145–152° C/0.01 mm Hg | 0.1 | 0.03 |
| (44₁) 4-Br, 2-C₂H₅-phenyl, N-CH₂-CH=CH₂ pyrrolidine | b.p. 148–152° C/0.01 mm Hg | 0.3 | 0.1 |
| (45₁) 2-Br, 4-Cl-phenyl, N-CH₂-CH=CH₂ pyrrolidine | b.p. 156–162° C/0.2 mm Hg | 0.1 | 0.01 |

Table 2-continued

In-vitro test for ovicidal effect on ticks

| Active compound | Physical constant | Ovicidal effect against *Boophilum,* ○ Biarra strain | |
|---|---|---|---|
| | | 100% Inhibition with the stated concentration of active compound | > 50% Inhibition (% by weight) |
| (46₁) 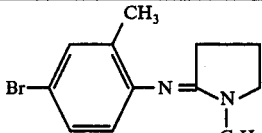 | b.p. 157–161° C/0.2 mm Hg | 0.3 | 0.2 |
| (47₁) 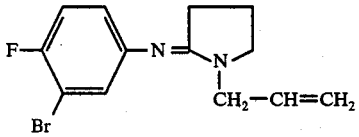 | b.p. 149–154° C/0.03 mm Hg | 0.1 | 0.08 |

EXAMPLE 3

In-vivo test against ticks on cattle 3 parts of the particular active compound are mixed with 7 parts of a mixture of equal parts by weight of ethyleneglycol monomethyl ether and nonylphenyl polyglycol ether. The emulsion concentrate so obtained is diluted with water to the application concentration desired in each case.

Cattle which have been infected (12 times at intervals of 2 days) with resistant larvae of ticks of the species *Boophilus microplus,* Biarra strain, are sprayed on the 24th day after the first infection with the preparation of the given active compound so obtained.

The effect of the preparation of the given active compound is determined by ascertaining the number of adult female ticks which have reached development on the treated cattle and later lay viable eggs. This number is compared with the number of adult femal ticks which have reached development on untreated cattle. The more effective a compound, the fewer female ticks which reach development after treatment and lay viable eggs.

As a measure of the intensity of the infestation before treatment, there is used the number of adult females which reach development in the case of the treated and untreated animals in the last three days before the time of treatment.

The particular active compounds tested and the results obtained can be seen from the following Table 3:

Table 3

In-vivo-test against ticks on cattle

| Active compound | Concentration of active compound in % | Days before treatment −2−1 0 | Number of female adult ticks which reach development on the cattle |||||||| Total number in 1-21 treatment days |
|---|---|---|---|---|---|---|---|---|---|---|
| | | | Days after treatment ||||||| |
| | | | +1+2+3 | +4+5+6 | +7+8+9 | +10+11+12 | +13+14+15 | +16+17+18 | +19+20+21 | |
| Untreated control animal | | 966 | 644 | 731 | 1313 | 1360 | 535 | 389 | 216 | 6154 |
| (1₂) 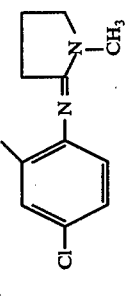 | 0.3<br>0.4<br>0.5 | 1012<br>1353<br>1428 | 0<br>0<br>0 | 1<br>0<br>0 | 119<br>72<br>1 | 55<br>74<br>7 | 33<br>31<br>3 | 4<br>6<br>1 | 0<br>0<br>0 | 212<br>183<br>12 |
| (7₂) 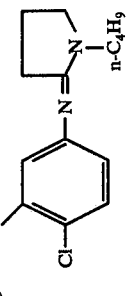 | 0.3 | 231 | 3 | 1 | 0 | 11 | 1 | 2 | 0 | 18 |
| (4₂) 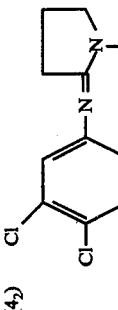 | 0.3 | 262 | 0 | 0 | 7 | 6 | 4 | 0 | 0 | 17 |

EXAMPLE 4

In-vitro test for ovicidal and adulticidal effect on ticks

The ovicidal effect is determined as stated in Example 1.

In addition, the adulticidal effectiveness of the preparation of the given active compound after 24 hours is determined by ascertaining the voluntary movement of limbs and bodies of the immersed adult ticks after stimulation with a fine needle compared with the voluntary movement of limbs and bodies of the untreated adult ticks. The effectiveness is stated in %, 100% meaning that no movements of any kind of the limbs and bodies were any longer detectable, and 0% signifying that the ticks moved limbs and bodies in normal manner.

The adulticidal effect, of the particular active compounds in the concentrations stated, corresponds always to the ovicidal effect, with the exception of those cases which are designated as "not adulticidal".

Table 4
In-vito test for ovicidal and adulticidal effect on ticks

| Active compound | Physical constant | Adulticidal and ovicidal effect against *Boophilus, Biarra* strain | |
|---|---|---|---|
| | | 100% | 50% |
| | | Inhibition with the stated concentration of active compound in % by weight | |
| (48₁) 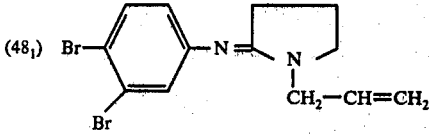 | b.p. 186 – 193° C/0.04 mm Hg | 0.1 | 0.05 |
| (49₁) 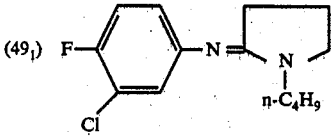 | b.p. 150 – 155° C/0.2 mm Hg | 0.1 | 0.03 |
| (50₁) 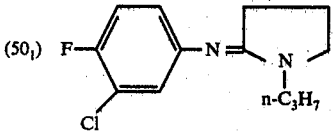 | b.p. 138 – 145° C/0.05 mm Hg | 0.1 | 0.03 |
| (51₁) 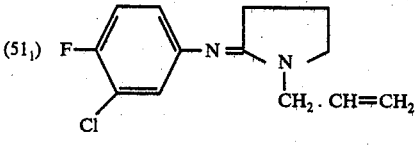 | b.p. 138 – 145° C/0.1 mm Hg | 0.1 | 0.08 |
| (52₁) 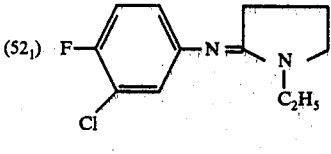 | b.p. 130 – 135° C/0.2 mm Hg | 0.3 | 0.1 |
| (53₁) 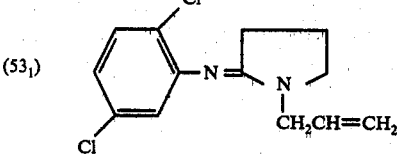 | b.p. 158 – 163° C/1.0 mm Hg | 0.1 | 0.03 |
| | | not adulticidal | |
| (54₁) 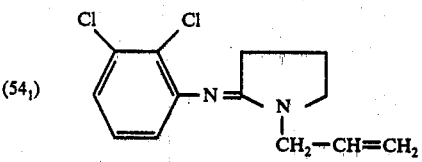 | b.p. 167 – 172° C/0.7 mm Hg | 0.01 | 0.008 |
| | | not adulticidal | |

Table 4-continued
In-vitro test for ovicidal and adulticidal effect on ticks

| Active compound | Physical constant | Adulticidal and ovicidal effect against *Boophilus, Biarra* strain 100% Inhibition with the stated concentration of active compound in % by weight | 50% |
|---|---|---|---|
| (55₁) 4-Cl, 3-Br-C₆H₃-N=C(pyrrolidine)-CH₂-CH=CH₂ | b.p. 168 – 174° C/0.3 mm Hg | 0.1 | 0.05 |
| (56₁) 4-Cl, 3-Br-C₆H₃-N=C(pyrrolidine)-n-C₄H₉ | b.p. 184 – 191° C/0.2 mm Hg | 0.1 | 0.03 |
| (57₁) 4-Cl, 3-Br-C₆H₃-N=C(pyrrolidine)-n-C₃H₇ | b.p. 179 – 185° C/0.6 mm Hg | 0.3 | 0.1 |
| (58₁) 4-Cl, 3-Br-C₆H₃-N=C(pyrrolidine)-C₂H₅ | b.p. 175 – 183° C/0.7 mm Hg | 0.1 | 0.05 |
| (59₁) 2-Cl, 4-F-C₆H₃-N=C(pyrrolidine)-n-C₄H₉ | b.p. 139 – 142° C/0.5 mm Hg | 0.03 | 0.01 |
| (60₁) 2-Cl, 4-F-C₆H₃-N=C(pyrrolidine)-CH₂.CH=CH₂ | b.p. 133 – 136° C/0.8 mm Hg | 0.1 | 0.03 |
| | | not adulticidal | |
| (61₁) 2-Cl, 4-F-C₆H₃-N=C(pyrrolidine)-n-C₃H₇ | b.p. 131 – 134° C/0.6 mm Hg | 0.1 | 0.03 |
| | | not adulticidal | |
| (62₁) 2,4,5-Cl₃-C₆H₂-N=C(pyrrolidine)-CH₂-CH=CH₂ | b.p. 186 – 190° C/1.5 mm Hg | 0.03 | 0.02 |
| | | not adulticidal | |
| (63₁) 3,4-Cl₂-C₆H₃-N=C(pyrrolidine)-CH₂-CH=CH-CH₃ | b.p. 171 – 176° C/0.2 mm Hg | 0.01 | 0.03 |

Table 4-continued

In-vitro test for ovicidal and adulticidal effect on ticks

| Active compound | Physical constant | Adulticidal and ovicidal effect against *Boophilus, Biarra* strain | |
|---|---|---|---|
| | | 100% | 50% |
| | | Inhibition with the stated concentration of active compound in % by weight | |
| (64₁) 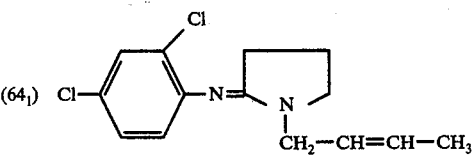 | b.p. 173 – 177° C/0.5 mm Hg | 0.01 | 0.03 |
| (65₁) 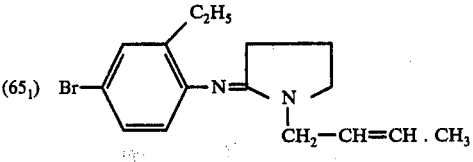 | b.p. 161 – 167° C/0.3 mm Hg | not adulticidal 0.1 | 0.05 |
| (66₁) 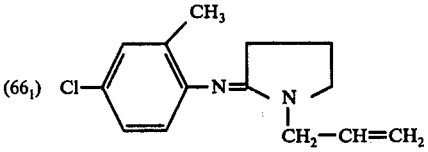 | b.p. 155 – 162° C/0.3 mm Hg | not adulticidal 0.03 | 0.02 |
| (67₁) 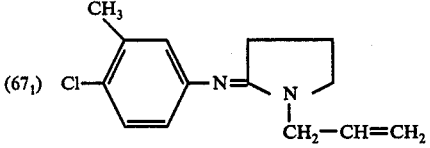 | b.p. 156 – 161° C/0.2 mm Hg | not adulticidal 0.03 | 0.02 |
| (68₁) 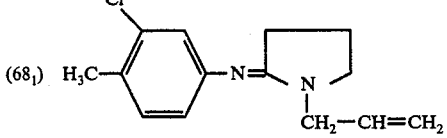 | b.p. 162 – 166° C/0.8 mm Hg | 0.03 | 0.01 |

EXAMPLE 5

The results below were obtained in a similar manner to those in accordance with Example 4.

Table 5

In-vitro test for ovicidal and adulticidal effect on ticks

| Active compound | Physical constant | Adulticidal and ovicidal effect against *Boophilus, Biarra* strain | |
|---|---|---|---|
| | | 100% | 50% |
| | | Inhibition with the stated concentration of active compound in % by weight | |
| (69₁) 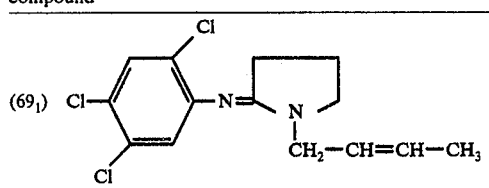 | b.p. 174 – 179° C/0.5 mm Hg | 0.1 | 0.03 |

Table 5-continued
In-vitro test for ovicidal and adulticidal effect on ticks

| Active compound | Physical constant | Adulticidal and ovicidal effect against *Boophilus, Biarra* strain | |
|---|---|---|---|
| | | 100% | 50% |
| | | Inhibition with the stated concentration of active compound in % by weight | |
| (70₁) 3-Cl, 4-CH₃-phenyl-N=pyrrolidine-CH₂-CH=CH-CH₃ | b.p. 159 – 166° C/0.5 mm Hg | 0.1 | 0.008 |
| (71₁) 3-CH₃, 4-Cl-phenyl-N=pyrrolidine-CH₂-CH=CH-CH₃ | b.p. 161 – 167° C/0.5 mm Hg | 0.03 | 0.02 |
| (72₁) 2-CH₃, 4-Cl-phenyl-N=pyrrolidine-CH₂-CH=CH-CH₃ | b.p. 157 – 161° C/0.3 mm Hg | 0.01 | 0.008 |
| (73₁) 3,4-diCl-phenyl-N=pyrrolidine-CH₂-C(CH₃)=CH₂ | b.p. 166 – 172° C/0.4 mm Hg | 0.1 | 0.03 |
| (74₁) 2,4-diCl-phenyl-N=pyrrolidine-CH₂-C(CH₃)=CH₂ | b.p. 156 – 162° C/0.2 mm Hg | 0.03 | 0.01 |
| (75₁) 2,4,5-triCl-phenyl-N=pyrrolidine-CH₂-C(CH₃)=CH₂ | b.p. 187 – 193° C/0.1 mm Hg | 0.3 | 0.1 |
| (76₁) 2-CH₃, 4-Cl-phenyl-N=pyrrolidine-CH₂-C(CH₃)=CH₂ | b.p. 152 – 158° C/0.5 mm Hg | 0.03 | 0.02 |
| (77₁) 4-CH₃, 3-Cl-phenyl-N=pyrrolidine-CH₂-C(CH₃)=CH₂ | b.p. 155 – 161° C/0.3 mm Hg | 0.1 | 0.03 |
| (78₁) 4-Cl, 3-CH₃-phenyl-N=pyrrolidine-CH₂-C(CH₃)=CH₂ | b.p. 154 – 161° C/0.3 mm Hg | 0.1 | 0.01 |
| (79₁) 3,4-diCl-phenyl-N=pyrrolidine-CH₂-CH₂-CH=CH₂ | b.p. 162 – 167° C/0.5 mm Hg | 0.3 | 0.1 |

Table 5-continued
In-vitro test for ovicidal and adulticidal effect on ticks

| Active compound | Physical constant | Adulticidal and ovicidal effect against *Boophilus, Biarra* strain 100% / 50% Inhibition with the stated concentration of active compound in % by weight | |
|---|---|---|---|
| (80₁) 4-CH₃-3-Cl-phenyl, N-CH₂-CH₂-CH=CH₂ pyrrolidine | b.p. 160 – 166° C/0.5 mm Hg | 0.03 | 0.02 |
| (81₁) 4-Cl-2-CH₃-phenyl, N-CH₂-CH₂-CH=CH₂ pyrrolidine | b.p. 149 – 153° C/0.5 mm Hg | 0.01 | 0.008 |
| (82₁) 3-Br-4-CH₃-phenyl, N-CH₂-CH=CH₂ pyrrolidine | b.p. 165 – 170° C/0.8 mm Hg | 0.1 | 0.03 |
| (83₁) 3-Br-4-CH₃-phenyl, N-C₄H₉(n) pyrrolidine | b.p. 168 – 172° C/0.8 mm Hg | 0.03 | 0.02 |
| (84₁) 4-Br-3-CH₃-phenyl, N-CH₂-CH=CH₂ pyrrolidine | b.p. 162 – 166° C/0.5 mm Hg | 0.1 | 0.03 |
| (85₁) 4-Br-3-CH₃-phenyl, N-C₄H₉(n) pyrrolidine | b.p. 163 – 168° C/0.4 mm Hg | 0.1 | 0.05 |

The following further examples are set forth to illustrate, without limitation, the manner of producing the instant compounds according to the present invention:

EXAMPLE 6

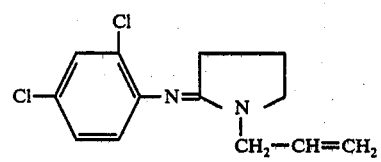

(86₁)

60 g 2,4-dichloro-aniline and 51 g N-allylpyrrolidone-(2) are dissolved in 300 g toluene, and 53 g phosphorus oxychloride are added dropwise. The mixture is then heated under reflux until evolution of hydrogen chloride has ended (3–4 hours). The mixture upon cooling is poured into ice water and excess solution of sodium hydroxide, and the toluene solution is dried over potassium carbonate and fractionally distilled.

An oil, b.p. 160°–164°/0.8 mm Hg, is obtained.

Yield: 82 g of 1-(α-allyl)-2-(2′,4′-dichloro-phenylimino)-pyrrolidine.

The toxicity determined on the mouse is: orally, 500 mg/kg; subcutaneously, 500 mg/kg (highest survived doses).

All of the other compounds of the present invention are prepared in the same manner, as the artisan will appreciate. For example, the following compounds are produced in a similar manner:

1-ethyl-2-(2′,4′,5′-trichloro-phenylimino)-pyrrolidine,
1-ethyl-2-(3′,4′-dichloro-phenylimino)-pyrrolidine,
1-tert.-butyl-2-(2′-methyl-4′-chloro-phenylimino)-pyrrolidine,
1-(α-allyl)-2-(2′,4′-dibromo-phenylimino)-pyrrolidine; and
1-(α-allyl)-2-(3′-bromo-4′-fluoro-phenylimino)-pyrrolidine.

It will be realized that all of the foregoing compounds contemplated by the present invention possess the desired selective pesticidal, especially parasiticidal, i.e. animal acarid ectoparasiticidal, properties for combating parasites, especially animal acarid ectoparasites, and that such compounds have only a very slight toxicity toward warm-blooded creatures.

It will be appreciated that the instant specification and examples are set forth by way of illustration and not limitation, and that various modifications and changes may be made without departing from the spirit and scope of the present invention.

What is claimed is:

1. A compound selected from the group consisting of

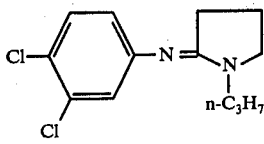

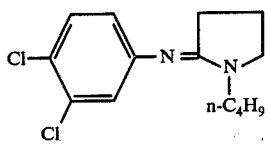

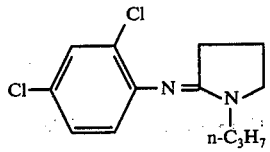

and

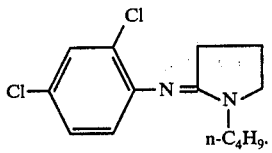

2. A compound according to claim 1 wherein such compound is

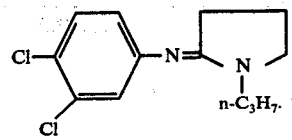

3. A compound according to claim 1 wherein such compound is

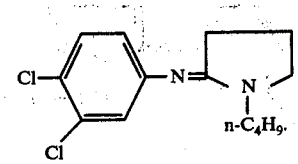

4. A compound according to claim 1 wherein such compound is

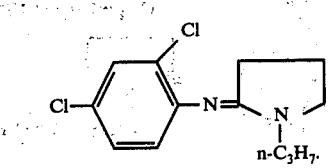

5. A compound according to claim 1 wherein such compound is

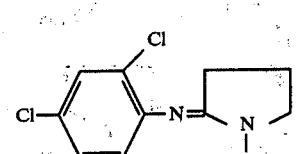

* * * * *